United States Patent [19]

Rosa et al.

[11] Patent Number: 4,753,879
[45] Date of Patent: Jun. 28, 1988

[54] MODIFIED TISSUE PLASMINOGEN ACTIVATORS

[75] Inventors: Joseph J. Rosa; Margaret D. Rosa, both of Winchester, Mass.

[73] Assignee: Biogen N.V., Curacao, Netherlands Antilles

[21] Appl. No.: 644,537

[22] Filed: Aug. 27, 1984

[51] Int. Cl.⁴ .......................... C12N 1/20; C12N 1/00; C07H 17/00
[52] U.S. Cl. .................... 435/172.3; 435/91; 435/253; 435/212; 435/215; 435/320; 536/27; 935/10; 935/14; 935/29; 935/73
[58] Field of Search ............... 435/68, 70, 172.3, 212, 435/253, 226, 254, 255, 317, 91, 240; 536/27; 935/10, 14, 27, 41, 50, 51, 67, 68, 69, 70, 72, 73

[56] References Cited

U.S. PATENT DOCUMENTS

| | | | |
|---|---|---|---|
| 3,555,000 | 1/1971 | Wagner | 260/112 |
| 3,904,480 | 9/1975 | Hull et al. | 195/66 |
| 3,998,947 | 12/1976 | D'Hinterland et al. | 424/105 |
| 4,190,574 | 2/1980 | Svendsen | 260/112.5 R |
| 4,232,124 | 11/1980 | Mann | 435/212 |
| 4,245,051 | 1/1981 | Reich et al. | 435/212 |
| 4,278,762 | 7/1981 | Svendsen | 435/13 |
| 4,314,994 | 2/1982 | D'Hinterland et al. | 424/95 |
| 4,317,882 | 3/1982 | Horiguchi et al. | 435/212 |
| 4,328,314 | 5/1982 | Horiguchi et al. | 435/212 |
| 4,370,417 | 1/1983 | Hung et al. | 435/212 |
| 4,505,893 | 3/1985 | Mori et al. | 424/94 |

FOREIGN PATENT DOCUMENTS

| | | |
|---|---|---|
| 41766 | 12/1981 | European Pat. Off. . |
| 0093619 | 11/1983 | European Pat. Off. .............. 935/14 |
| 94720 | 11/1983 | European Pat. Off. . |
| 99126 | 1/1984 | European Pat. Off. . |
| 8303101 | 9/1983 | PCT Int'l Appl. . |
| 8401786 | 5/1984 | PCT Int'l Appl . |
| 8401960 | 5/1984 | PCT Int'l Appl . |
| 2122219 | 1/1984 | United Kingdom . |

OTHER PUBLICATIONS

Pennica et al., *Nature*, vol. 301, pp. 214–221, Jan. 1983.
Wiman et al. *Nature*, vol. 272, pp. 549–550, 1978.
Radcliffe, *Biochimica et Biophysica Acta*, vol. 743, pp. 422–430, Mar. 1983.
Jornval et al., *FEBS Letters*, vol. 156, No. 1, pp. 47–50, Jun. 1983.
Ichinose et al., *FEBS Letters*, vol. 175, No. 2, pp. 412–418, Oct. 1984.
Rijken et al., *J. Biol Chem*, vol. 256, No. 6, pp. 2920–2925, 1982.
Wallen et al., *Eur. J. Biochem*, vol. 32, pp. 681–686, May 1983.
T. Edlund et al., "Isolation of cDNA Sequences Coding for a Part of Human Tissue Plasminogen Activator", *Proc. Natl. Acad. Sci. U.S.A.*, 80, pp. 349–352 (1983).
G. Opdenakker et al., "Messenger RNA for Human Tissue Plasminogen Activator", *Eur. J. Biochem.*, 121, pp. 269–274 (1982).
M. Ranby et al., "Enzymatic Properties of the One-and Two-Chain Form of Tissue Plasminogen Activator", *Thromb. Rsch.*, 27, pp. 175–183 (1983).
D. Rijken and D. Collen, "Purification and Characterization of the Plasminogen Activator Secreted by Human Melanoma Cells in Culture", *J. Biol. Chem.*, 256, pp. 7035–7041 (1981).
W. Strassburger et al., "Adaptation of Plasminogen Activator Sequences to Known Protease Structures", *FEBS Letters*, 157, pp. 219–223 (1983).
D. Pennica, "Recent Progress in the Cloning of Human Tissue Plasminogen Activator Gene", Abstracts of the Sixth International Congress on Fibrinolysis, Jul. 20–23, 1982, reprinted in *Haemostasis*, 11/s1/82 (1982).

*Primary Examiner*—Thomas G. Wiseman
*Assistant Examiner*—Jayme A. Huleatt
*Attorney, Agent, or Firm*—James F. Haley, Jr.; Margaret A. Pierri

[57] ABSTRACT

Modified human tissue plasminogen activators, the DNA sequences coding on expression for them and methods of making them in hosts transformed with those DNA sequences. The single chain form of these modified human t-PAs, t-PA (Lys 277→X), has a longer half life than the single chain form of native, or recombinant, t-PA, yet, in the two chain form these modified t-PAs have substantially the same affinity for fibrin and substantially the same activity as the two chain form of native, or recombinant, t-PA.

21 Claims, 3 Drawing Sheets

FIG. 1

```
                                                              -1 +1
                                          MetGlyAlaArgSerTyrGlnValIle        5
                                          ATGGGAGCCAGATCTTACCAAGTGATC

CysArgAspGluLysThrGlnMetIleTyrGlnGlnHisGlnSerTrpLeuArgProVal                25
TGCAGAGATGAAAAAACGCAGATGATATACCAGCAACATCAGTCATGGCTGCGCCCTGTG

LeuArgSerAsnArgValGluTyrCysTrpCysAsnSerGlyArgAlaGlnCysHisSer                45
CTCAGAAGCAACCGGGTGGAATATTGCTGGTGCAACAGTGGCAGGGCACAGTGCCACTCA

ValProValLysSerCysSerGluProArgCysPheAsnGlyGlyThrCysGlnGlnAla                65
GTGCCTGTCAAAAGTTGCAGCGAGCCAAGGTGTTTCAACGGGGGCACCTGCCAGCAGGCC

LeuTyrPheSerAspPheValCysGlnCysProGluGlyPheAlaGlyLysCysCysGlu                85
CTGTACTTCTCAGATTTCGTGTGCCAGTGCCCCGAAGGATTTGCTGGGAAGTGCTGTGAA

IleAspThrArgAlaThrCysTyrGluAspGlnGlyIleSerTyrArgGlyThrTrpSer               105
ATAGATACCAGGGCCACGTGCTACGAGGACCAGGGCATCAGCTACAGGGGCACGTGGAGC

ThrAlaGluSerGlyAlaGluCysThrAsnTrpAsnSerSerAlaLeuAlaGlnLysPro               125
ACAGCGGAGAGTGGCGCCGAGTGCACCAACTGGAACAGCAGCGCGTTGGCCCAGAAGCCC

TyrSerGlyArgArgProAspAlaIleArgLeuGlyLeuGlyAsnHisAsnTyrCysArg               145
TACAGCGGGCGGAGGCCAGACGCCATCAGGCTGGGCCTGGGGAACCACAACTACTGCAGA

AsnProAspArgAspSerLysProTrpCysTyrValPheLysAlaGlyLysTyrSerSer               165
AACCCAGATCGAGACTCAAAGCCCTGGTGCTACGTCTTTAAGGCGGGGAAGTACAGCTCA

GluPheCysSerThrProAlaCysSerGluGlyAsnSerAspCysTyrPheGlyAsnGly               185
GAGTTCTGCAGCACCCCTGCCTGCTCTGAGGGAAACAGTGACTGCTACTTTGGGAATGGG

SerAlaTyrArgGlyThrHisSerLeuThrGluSerGlyAlaSerCysLeuProTrpAsn               205
TCAGCCTACCGTGGCACGCACAGCCTCACCGAGTCGGGTGCCTCCTGCCTCCCGTGGAAT
                                                                ↑R1
SerMetIleLeuIleGlyLysValTyrThrAlaGlnAsnProSerAlaGlnAlaLeuGly               225
TCCATGATCCTGATAGGCAAGGTTTACACAGCACAGAACCCCAGTGCCCAGGCACTGGGC

LeuGlyLysHisAsnTyrCysArgAsnProAspGlyAspAlaLysProTrpCysHisVal               245
CTGGGCAAACATAATTACTGCCGGAATCCTGATGGGGATGCCAAGCCCTGGTGCCACGTG

LeuLysAsnArgArgLeuThrTrpGluTyrCysAspValProSerCysSerThrCysGly               265
CTGAAGAACCGCAGGCTGACGTGGGAGTACTGTGATGTGCCCTCCTGCTCCACCTGCGGC
                     277
LeuArgGlnTyrSerGlnProGlnPheArgIleLysGlyGlyLeuPheAlaAspIleAla               285
CTGAGACAGTACAGCCAGCCTCAGTTTCGCATCAAAGGAGGGCTCTTCGCCGACATCGCC

SerHisProTrpGlnAlaAlaIlePheAlaLysHisArgArgSerProGlyGluArgPhe               305
TCCCACCCCTGGCAGGCTGCCATCTTTGCCAAGCACAGGAGGTCGCCCGGAGAGCGGTTC
```

FIG. 2

```
     LeuCysGlyGlyIleLeuIleSerSerCysTrpIleLeuSerAlaAlaHisCysPheGln      325
     CTGTGCGGGGGCATACTCATCAGCTCCTGCTGGATTCTCTCTGCCGCCCACTGCTTCCAG

GluArgPheProProHisHisLeuThrValIleLeuGlyArgThrTyrArgValValPro      345
     GAGAGGTTTCCGCCCCACCACCTGACGGTGATCTTGGGCAGAACATACCGGGTGGTCCCT

GlyGluGluGluGlnLysPheGluValGluLysTyrIleValHisLysGluPheAspAsp      365
     GGCGAGGAGGAGCAGAAATTTGAAGTCGAAAAATACATTGTCCATAAGGAATTCGATGAT
                                                         ↑ R1

AspThrTyrAspAsnAspIleAlaLeuLeuGlnLeuLysSerAspSerSerArgCysAla      385
     GACACTTACGACAATGACATTGCGCTGCTGCAGCTGAAATCGGATTCGTCCCGCTGTGCC

GlnGluSerSerValValArgThrValCysLeuProProAlaAspLeuGlnLeuProAsp      405
     CAGGAGAGCAGCGTGGTCCGCACTGTGTGCCTTCCCCGGCGGACCTGCAGCTGCCGGAC

TrpThrGluCysGluLeuSerGlyTyrGlyLysHisGluAlaLeuSerProPheTyrSer      425
     TGGACGGAGTGTGAGCTCTCCGGCTACGGCAAGCATGAGGCCTTGTCTCCTTTCTATTCG

GluArgLeuLysGluAlaHisValArgLeuTyrProSerSerArgCysThrSerGlnHis      445
     GAGCGGCTGAAGGAGGCTCATGTCAGACTGTACCCATCCAGCCGCTGCACATCACAACAT

LeuLeuAsnArgThrValThrAspAsnMetLeuCysAlaGlyAspThrArgSerGlyGly      465
     TTACTTAACAGAACAGTCACCGACAACATGCTGTGTGCTGGAGACACTCGGAGCGGCGGG

ProGlnAlaAsnLeuHisAspAlaCysGlnGlyAspSerGlyGlyProLeuValCysLeu      485
     CCCCAGGCAAACTTGCACGACGCCTGCCAGGGCGATTCGGGAGGCCCCCTGGTGTGTCTG

AsnAspGlyArgMetThrLeuValGlyIleIleSerTrpGlyLeuGlyCysGlyGlnLys      505
     AACGATGGCCGCATGACTTTGGTGGGCATCATCAGCTGGGGCCTGGGCTGTGGACAGAAG

AspValProGlyValTyrThrLysValThrAsnTyrLeuAspTrpIleArgAspAsnMet      525
     GATGTCCCGGGTGTGTACACAAAGGTTACCAACTACCTAGACTGGATTCGTGACAACATG

ArgPro
     CGACCGTGA   CCAGGAA      CACCCGACTC   CTCAAAAGCA   AATGAGATCC
     CGCCTCTTCT  TCTTCAGAAG   ACACTGCAAA   GGCGCAGTGC   TTCTCTACAG
     ACTTCTCCAG  ACCCACCACA   CCGCAGAAGC   GGGACGAGAC   CCTACAGGAG
     AGGGAAGAGT  GCATTTTCCC   AGATACTTCC   CATTTTGGAA   GTTTTCAGGA
     CTTGGTCTGA  TTTCAGGATA   CTCTGTCAGA   TGGGAAGACA   TGAATGCACA
     CTAGCCTCTC  CAGGAATGCC   TCCTCCCTGG   GCAGAAGTGG   CCATGCCACC
     CTGTTTTCGC  TAAAGCCCAA   CCTCCTGACC   TGTCACCGTG   AGCAGCTTTG
     GAAACAGGAC  CACAAAAATG   AAAGCATGTC   TCAATAGTAA   AAGAAACAAG
     AGATCT
```

MODIFIED TISSUE PLASMINOGEN ACTIVATORS

TECHNICAL FIELD OF INVENTION

This invention relates to modified tissue plasminogen activators, DNA sequences coding for them and processes for producing and using them. More particularly, this invention relates to modified tissue plasminogen activators that become enzymatically active only after proteolytic cleavage. As a result, the modified tissue plasminogen activators of this invention display a longer half-life and slower clearance from the blood than native, or previous recombinant produced, tissue plasminogen activators.

BACKGROUND ART

Acute vascular diseases, such as myocardial infarction, stroke, pulmonary embolism, deep vein thrombosis, peripheral arterial occlusion, and other blood system thromboses are major health risks. They are caused by either a partial, or total, occlusion of a blood vessel by a blood clot.

Accordingly, attempts have been, and continue to be made, to treat these diseases by the use of thrombolytic agents. Such agents dissolve the blood clot thereby removing it from the blood vessel and unblocking the flow of blood.

Because blood clots consist of fibrin, various attempts have been made to dissolve them using plasminogen activators, which are compounds that convert plasminogen, a blood plasma protein precursor, to plasmin, a proteolytic enzyme that degrades the fibrin network of a blood clot to form soluble products [D. Collen, *Thromb. Haemostasis*, 43, pp. 77–89 (1980); B. Wiman & D. Collen, *Nature*, 272, pp. 549–50 (1978)].

There are several compounds now available that may function as plasminogen activators in such treatments. These include: streptokinase, a bacterial protein, urokinase, a serine protease isolated from human urine, and two plasminogen activators, tissue-type plasminogen activator and urokinase-type plasminogen activator, that may be extracted from tissues and are produced in certain cells [E. Reich in *Proteases And Biological Control* (eds. E. Reich et al.), pp. 333–41 (Cold Spring Harbor Laboratory, New York) (1975)].*

* In this application the plasminogen activator nomenclature proposed at the XXVIII Meeting of the International Committee on Thrombosis and Hemostasis, Bergamo, Italy (July 27, 1983) will be used: tissue-type plasminogen activator ("t-PA") and urokinase-type plasminogen activator ("u-PA").

Each of these plasminogen activators has certain limitations. For example, streptokinase and urokinase do not have a high affinity for fibrin. As a result, they may convert both circulating and fibrin-bound plasminogen to plasmin. This may be a significant disadvantage, because not only is the plasmin formed in the circulating blood of marginal utility in dissolving blood clots, but it also may contribute to hemorrhagic potential by degrading various clotting factors, e.g., fibrinogen and Factor VIII. Urokinase-type plasminogen activator has similar disadvantages. Accordingly, neither streptokinase nor urokinase therapy is likely to be fully satisfactory in the treatment of vascular disease.

Tissue-type plasminogen activator ("t-PA"), on the other hand, has a higher affinity for fibrin than urokinase-type plasminogen activator [O. Matsuo et al., *Thromb. Haemostasis*, 45, pp. 225–29 (1981); C. Korninger et al., *Thromb. Haemostasis*, 46, pp. 561–65, 658–61, 662–65, (1981); M. Hoylaerts et al., *J. Biol. Chem.*, 257, pp. 2912–29 (1982)]. Moreover, some studies suggest that t-PA may selectively seek out and dissolve blood clots without the potential hemorrhagic side effects associated with other plasminogens and treatments based on them [FDC Reports, T & G-3-4 (Mar. 26, 1984)].

Therefore, attempts have been made to produce and to evaluate clinically human t-PA in thrombolytic agents and therapy. Such attempts are referred to, for example, in European patent application Nos. 93619 and 99126. Application No. 99126 refers to a thrombolytic composition said to contain a t-PA isolated from human kidneys and bood vessels. Application No. 93619 refers to human t-PA said to be produced through recombinant techniques. See also D. Pennica et al., "Coning And Expression Of Human Tissue-Type Plasminogen Activalor cDNA In *E.coli*", *Nature*, 301, pp. 214–221 (1983).

However, these native and recombinant t-PAs may also not be fully satisfactory in on-going therapy to dissolve blood clots, because they may be cleared from the blood faster than is desirable for optimum utility and effectiveness in therapy. For example, the half-life of native t-PA is about 3 minutes; the t-PA being cleared from the blood by a single passage through the liver. Therefore, very high, continuous dosage therapy must be employed. For example, it has been reported that doses of 80–100 mg of recombinant t-PA are now required. Therefore, plasminogen activators that are highly selective for fibrin, and also have extended lifetimes in the blood, would be more satisfactory and potentially more useful in thrombolytic agents and therapy.

SUMMARY OF THE INVENTION

The present invention solves the problems referred to by providing modified tissue plasminogen activators. These plasminogen activators are at least as selective for fibrin as native or unmodified t-PA. Yet, they also have an extended half-life in the blood, as compared to those native or unmodified t-PAs.

The present invention also provides DNA sequences coding for these modified t-PAs and methods of using those DNA sequences to produce those modified t-PAs for use in a wide variety of thrombolytic agents and vascular disease therapies.

Finally, the present invention provides various thrombolytic compositions containing the modified t-PAs of this invention and various methods of using those compositions in vascular disease therapy.

As will be apparent from the disclosure and examples to folow, the modified t-PAs of this invention are characterized by the formula t-PA (Lys 277→X), wherein X is selected from the group consisting of one or more amino acid substitutions, modifications or deletions that prevents any substantial complexation between amino acid 277 and amino acid 194 in the single chain form of that t-PA. Preferably, X is selected from the group consisting of at least one amino acid residue, the residues being characterized by the absence of any substantial positive charge, at least one amino acid deletion that removes any substantial positive charge from the 277 lysine in the single chain form of that t-PA, and at least one amino acid modification that removes any substantial positive charge from the 277 lysine in the single chain form of that t-PA. More preferably, X is selected from the group consisting of the amino acid residues Phe, Leu, Ile, Met, Val, Ser, Pro, Thr, Ala, Tyr, Asp, Glu, Cys, Trp, and Gly. Most preferably, X is isoleucine (Ile).

BRIEF DESCRIPTION OF THE DRAWINGS

FIGS. 1–2 depict the t-PA coding sequence that characterizes plasmid pTPA25.

BEST MODE OF CARRYING OUT THE INVENTION

Figure 3:
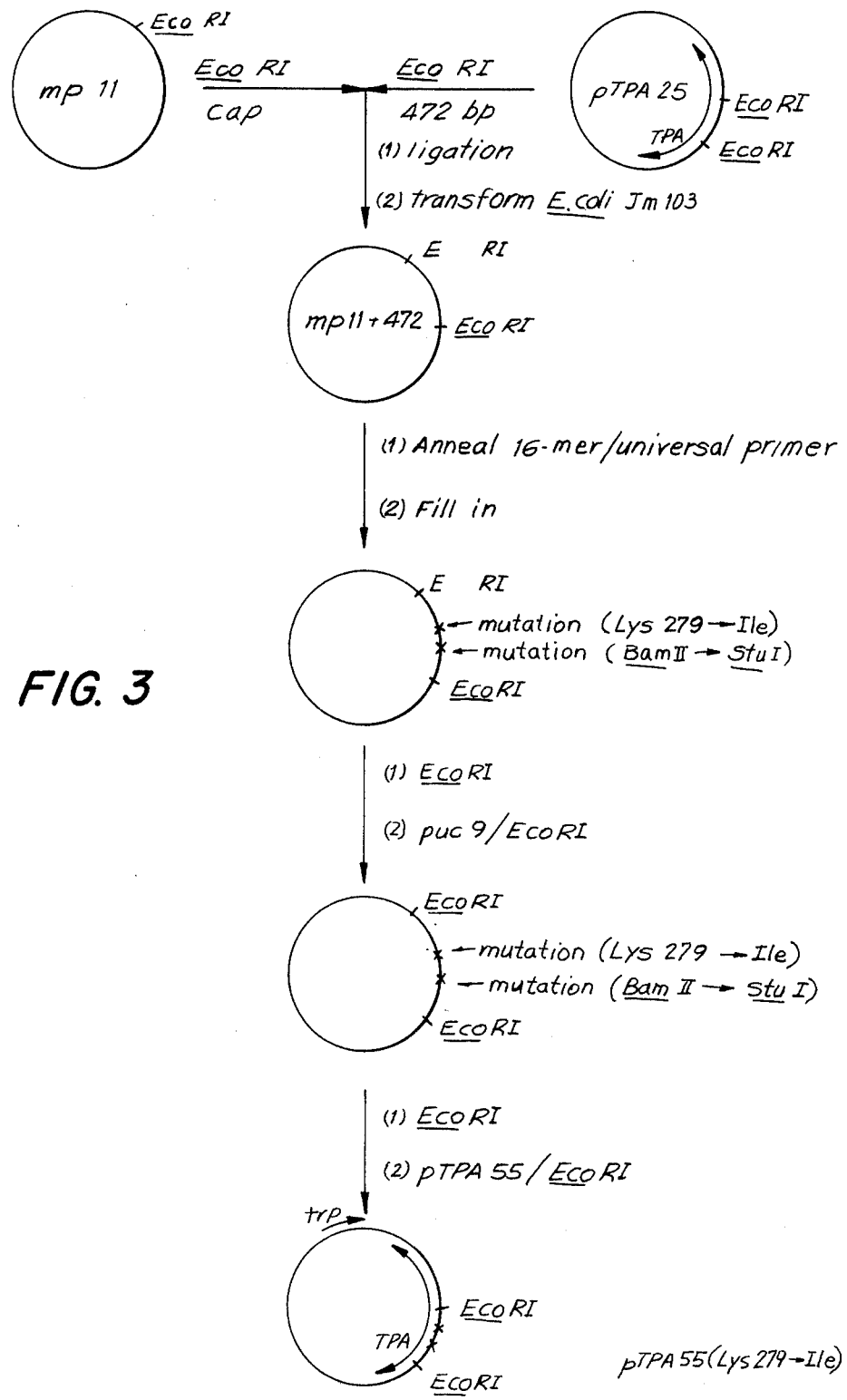
FIG. 3 depicts in schematic outline one embodiment of a method of preparing a DNA sequence encoding a modified t-PA in accordance with this invention.

In order that the invention herein described may be more fully understood, the following definitions and detailed description are set forth.

"Tissue Plasminogen Activator" or "t-PA" as used in this application and claims is a protein with the bioogical activity (e.g., it is capable in at least the two chain form of catalyzing the conversion of plasminogen to plasmin and binds to fibrin) of human tissue plasminogen activator, for example, that isolated from Bowes melanoma cells (D. C. Rijken and D. Collen, *J. Biol Chem.*, 256, pp. 2035–41 (1981) or Hela cells (W. D. Schleuning and E. Reich, Abstract, 6th Conference on Fibrinolysis, Lausanne, Switzerland, July 22–25, 1982). "t-PA" exists in both a single and two chain form. In native "t-PA", the single chain form has substantial activity. The two chain form is also active.

"t-PA" within the above definition includes proteins that have the amino acid sequence of native human tissue plasminogen activator. It also includes proteins that include an amino terminal methionine, e.g., f-Met-t-PA, and proteins that are characterized by other amino terminal amino acid deletions or additions so long as those proteins substantially retain the activity of t-PA.

"t-PA" within the above-definition also includes natural allelic variations that may exist and occur from individual to individual. Furthermore, it includes t-PAs whose degree and location of glycosylation, or other post-translation modifications, may vary depending on the cellular environment of the producing host or tissue. It also includes both native and recombinant t-PAs.

"t-PA (Lys 277→X)" as used in this application and claims is a modified tissue plasminogen activator within the above definition, wherein X is selected from the group consisting of one or more amino acid substitutions, modifications or deletions that prevents any substantial complexation between amino acid 277 and amino acid 194 in the single chain form of that t-PA. Preferably, X is selected from the group consisting of at least one amino acid residue, the residues being characterized by the absence of any substantial positive charge, at least one amino acid deletion that removes any substantial positive charge from the 277 lysine in the single chain form of that t-PA, and at least one amino acid modification that removes any substantial positive charge from the 277 lysine in the single chain form of that t-PA. More preferably, X is any amino acid other than His, Arg and Lys. Most preferably, X is isoleucine (Ile). For example, t-PA (Lys 277→Ile) has an isoleucine residue, instead of a lysine residue, at position 277. And t-PA (Lys 277→ΔLys) has a deletion of the lysine residue at position 277.

As compared to native t-PA, the preferred modified t-PAs of this invention (t-PA (Lys 277→X)) are characterized by a single amino acid change—lysine to an amino acid residue not characterized by a positive charge, e.g., all residues except His, Arg and Lys, i.e., Phe, Leu, Ile, Met, Val, Ser, Pro, Thr, Ala, Glu, Cys, Trp, and Gly—at amino acid 277. See FIG. 1. Most preferably, the amino acid residue at position 277 is Ile because with that 277 residue our modified t-PA is identical to urokinase at position 277.

We believe that these amino acid modifications result in the single chain form of our modified t-PA having a longer half-life in the blood stream than single chain, unmodified, native or recombinant, t-PA. At the same time, this modification does not significantly affect the affinity of the two chain form of our modified t-PA for fibrin or its activity in dissolving blood clots.

While not wishing to be bound by theory, we believe that the single chain form of our modified t-PAs has a longer half-life than the single chain form of native, or recombinant, t-PA, because our modified t-PAs are substantially inactive in the single chain form. Accordingly, our modified t-PAs (in the single chain form) cannot indiscriminately bind to protease inhibitors and thereby should avoid the rapid blood clearance caused by such inhibitor binding. Instead, our modified t-PAs are activated only at the site of the clot, where proteolytic cleavage enables them to catalyze the conversion of plasminogen to plasmin, which then degrades the blood clot. The single chain form of our modified t-PAs thus displays a substantially longer half-life in the blood stream than unmodified single chain native or recombinant t-PA. However, after activation by cleavage, our modified t-PAs display substantially the same affinity for fibrin and substantially the same activity in dissolving blood clots as the two chain form of native or recombinant t-PA.

Again, while not wishing to be bound by theory, we believe that the single chain form of our modified t-PAs has a longer half-life than unmodified single chain native, or recombinant, t-PA because our replacement of the Lys-277 with at least another amino acid residue or deletion that is not characterized by a positive charge, prevents the former potential complexation between the Lys-277 residue (through its ε-amino group) and the Asp 194 residue. We believe that this complexation tends to unblock the active site of t-PA and thereby to activate substantial amounts of the single chain form of native t-PA [P. Wallen et al., "Purification And Characterization of A Melanoma Cell Plasminogen Activator", *Eur. J. Biochem.*, 132, pp. 681–86 (1983)]. In our more preferred embodiments, we believe that the replacement of the 277 Lys residue with any other amino acid residue, except His, Arg or Lys, and most preferably its replacement by the residue Ile results in this improvement over unmodified nature or recombinant t-PA. However, it should also be understood that other modifications, replacements and deletions at the 277 Lysine residue that prevent this 277-194 amino acid complexation are also useful in the modified t-PA's of our invention.

To prepare the modified t-PAs of this invention, we prefer to modify the DNA sequence encoding native t-PA and then to employ that modified DNA sequence to produce a modified t-PA of this invention. Of course, it should be understood that our modifications could also have been effected at the protein level. However, that latter process is less preferred.

We also prefer to employ site-directed mutagenesis to effect the amino acid residue replacement or deletion at position 277. For example, we can use that method to replace the 277 Lys with one or more residues that interfere with complexation of that amino acid with the residue of position 194. We can also use that method to delete the lysine. In the preferred embodiment of this invention, we effect a codon mutation at amino acid 277 from one coding for lysine to one coding for a non-positively charged amino acid residue, e.g., all amino acid residues, except His, Arg and Lys. Most preferably, we use this codon mutation method to make the residue at 277 isoleucine. Again, however, it should be understood that a wide variety of mutational or codon replacement strategies, as well as other replacement and deletion methods known in the art, could also be employed. For example, the t-PA DNA sequence, or a portion of it, could be cut by restriction endonucleases and a synthetic or other DNA fragment coding for the desired residues or deletions substituted for the excised fragment.

Having prepared a DNA sequence carrying the desired replacement or deletion we employ it in a variety of expression vectors and hosts to produce the modified t-PA encoded by it. For example, any of a wide variety of expression vectors are useful in expressing the modified t-PA coding sequences of this invention.

These include, for example, vectors consisting of segments of chromosomal, non-chromosomal and synthetic DNA sequences, such as various known derivatives of SV40, known bacterial plasmids, e.g., plasmids from *E.coli* including col E1, pCR1, pBR322, pMB9 and their derivatives, wider host range plasmids, e.g., RP4, phage DNAs, e.g., the numerous derivatives of phage λ, e.g., NM 989, and other DNA phages, e.g., M13 and Filamenteous single stranded DNA phages, yeast plasmids such as the 2μ plasmid or derivatives thereof, and vectors derived from combinations of plasmids and phage DNAs, such as plasmids which have been modified to employ phage DNA or other expression control sequences. In the preferred embodiments of this invention, we employ SV40, *E.coli* and yeast vectors.

In addition, any of a wide variety of expression control sequences—sequences that control the expression of a DNA sequence when operatively linked to it—may be used in these vectors to express the DNA sequence of this invention. Such useful expression control sequences, include, for example, the early and late promoters of SV40, the lac system, the trp system the TAC or TRC system, the major operator and promoter regions of phage λ, the control regions of fd coat protein, the promoter for 3-phosphoglycerate kinase or other glycolytic enzymes, the promoters of acid phosphatase, e.g., Pho5, the promoters of the yeast α-mating factors, and other sequences known ro control the expression of genes of prokaryotic or eukaryotic cells or their viruses, and various combinations thereof. Again, in the preferred embodiments of this invention, we employ SV40, *E.coli* and yeast expression control sequences. Most preferably we employ SV40-derived expression control sequences in CHO host cells and the TRC system in *E.coli* host cells.

A wide variety of microbial hosts are also useful in producing the modified t-PAs of this invention. These hosts include, for example, bacteria, such as *E.coli*, Bacillus and Streptomyces, fungi, such as yeasts, and animal, such as CHO cells, and plant cells in tissue culture. In the preferred embodiments of this invention, we prefer *E.coli* host cells, particularly *E.coli* SG20251, animal host cells, particularly CHO cells, and Streptomyces host cells.

It should of course be understood that not all expression vectors and expression systems will function in the same way to express the modified DNA sequences of this invention and to produce our modified t-PAs. Neither will all hosts function equally well with the same expression system. However, one of skill in the art may make a selection among these vectors, expression control sequences and hosts without undue experimentation without departing from the scope of this invention. For example, in selecting a vector, the host must be considered because the vector must replicate in it. The vector's copy number, the ability to control that copy number, and the expression of any other proteins encoded by the vector, such as antibiotic markers, should also be considered.

In selecting an expression control sequence, a variety of factors should also be considered. These include, for example, the relative strength of the system, its controllability, its compatibility with the DNA sequence encoding the modified t-PAs of this invention, particularly as regards potential secondary structures. Hosts should be selected by consideration of their compatibility with the chosen vector, the toxicity of our modified t-PAs to them, their ability to secrete mature products, their ability to fold proteins correctly, their fermentation requirements, the ease of the purification of our modified t-PAs from them and safety.

Within these parameters one of skill in the art may select various vector/expression control system/host combinations that will produce useful amounts of our modified t-PAs on fermentation. For example, in one preferred embodiment of this invention, we use an *E.coli* TRC system in *E.coli* SG 20251. In another, we use CHO, DHFR$^-$ cells, SV40-derived promoters and amplification of plasmid carried dhfr and t-PA by MTX (methotrexate).

The modified t-PAs produced in these fermentations may be purified by a variety of conventional steps and strategies. Useful purification steps include those used to purify unmodified recombinant t-PAs. For example, in systems that do not excrete the modified t-PAs, we break the cells, pellet the t-PA, extract and solubilize the t-PA using a chaotropic agent, e.g., GuHCl, refold the t-PA by dilution into a buffer—the refolded t-PA fraction remaining soluble in the buffer, and purify further, if necessary, by chromatography, e.g., SP-Sephadex, or precipitation.

After purification the modified t-PAs of this invention are useful in compositions and methods for vascular disease therapy and in a variety of thrombolytic agents. Preferably, the single chain form of our modified t-PA is used in these agents, because it displays a longer half life than the two chain form.

For example, the modified t-PAs of this invention may be formulated using known methods to prepare pharmaceutically useful compositions. Such compositions will preferably include at least one pharmaceutically acceptable carrier. See, e.g., Remington's Pharmaceutical Sciences (E. W. Martin). The resulting formulations will contain an amount of modified t-PA effective in the host after activation to reduce blood clots.

Various dosage forms may be employed to administer these modified t-PA-containing compositions. For example, parenteral administration may be used for patients suffering from cardiovascular diseases or conditions. The dosage and dose rate will depend on a variety of factors. However, they are similar to those currently used with other cardiovascular, thrombolytic agents, e.g., about 440 IU/Kg body weight as an intravenous priming dose followed by a continuous intravenous infusion at 440 IU/Kg/hr for several hours. Because our modified t-PAs display a longer half-life as compared to unmodified recombinant and native t-PA, our dosage amounts are well below the 80-100 mg amounts used in present therapy with those products.

We provide the following example of preparing a modified t-PA DNA sequence of this invention and of producing a modified t-PA coded for by that DNA sequence for illustrative purposes only.

EXAMPLE

Referring now to FIGS. 1-2, we have depicted therein the t-PA coding sequence that characterizes plasmid pTPA25. This plasmid is characterized by an ATG start codon, as part of an NcoI restriction site, directly in front of the GGA codon coding for the glycine residue at position -3 (FIG. 1) of t-PA. It also contains the complete cDNA sequence coding for mature t-PA and a portion of the 5'-non-coding region.

As depicted in FIG. 3, we restricted pTPA25 with excess EcoRI and isolated the 472 base pair fragment containing base pairs 803-1275 (residues 205-361) of the t-PA cDNA sequence of pTPA25 and subcloned it into M13 mp11 (an M13 phage vector; PL Biochemicals) that we had restricted with excess EcoRI and treated with calf alkaline phosphatase ("CAP") (Boehringer-Mannheim) to remove the 5' phosphate groups to prevent re-circularization of the plasmid and phage. For this subcloning, we used the following ligation conditions: 66 mM Tris-HCl (pH 8), 10 mM MgCl2, 1 mM DDT, 1 mM ATP ("1×ligase buffer") overnight. We then transformed competent E.coli JM103 [J. Messing et al., *Nucleic Acids Res.*, 9, pp. 309-21 (1981)] with the resulting vector and selected the white plaques using X-gal plates.

We then isolated the single-stranded DNA secreted by the selected cells by centrifugation, added PEG (6000) to the supernatant, collected the precipitate, extracted it with phenol-CHCl3 (50:50), precipitated the DNA with ethanol, and collected it by centrifugation.

We next annealed two synthetic primers to the single-stranded DNA. The first oligonucleotide was a 16-mer: 3' TAG TAT CCT CCG GAG A 5'. It contained two mutations as compared to the t-PA cDNA sequence of pTPA25. The first mutation changed the codon AAA (at the 277 lysine residue) to ATA (isoleucine). The second mutation changed the codon GGG (at the 279 glycine residue) to GGC (glycine). This mutation resulted in a BanII restriction site being modified into a StuI restriction site, while leaving the amino acid (glycine) the same. We effected this second mutation solely to make screening for mutated sequences easier and quicker. The second oligonucleotide primer was a 17-mer universal sequencing primer (N.E. Biolabs No. 1211): 3'GTAAAACGACGGCCAT 5'.

For annealing, we used 1×ligation buffer (without ATP), 100 pmol of 16-mer, 30 ng of the universal primer, 2 μg of the single-stranded DNA and water to 40 μl. We annealed at 65° C. for 1 min, then at room temperature for 10 min, added 1 μl 10×ligase buffer (without ATP), 5 μl 10 mM ATP; 1 μl 10 mM dNTPs, 0.5 μl DNA polymerase I, Klenow fragment (2 units), 1 μl T4 DNA ligase (N.E. Biolabs) and maintained the reaction mixture at 15° C. for 2 h to make double-stranded DNA.

We digested the resulting double-stranded DNA with EcoRI, isolated the 472 base pair EcoRI fragment, as before, and subcloned it under the same conditions used with mp11 into pUC9 [J. Vieira and J. Messing. "The pUC Plasmids, An M13 mp11-Derived System For Insertion Mutagenesis And Sequencing With Synthetic Universal Primers", *Gene*, 19, pp. 259-62 (1982)] that we had restricted with EcoRI and treated with CAP to remove the 5' phosphates to prevent recircularization. We then transformed competent E.coli JM83 (Messing et al., supra) with the resulting vector and again selected the white colonies (X-gal plates, supplemented with 50 μg/ul ampicillin).

We picked the selected colonies into microtiter dishes (containing L-broth supplemented with 50 μg/ul ampicillin), plated them onto nitrocellulose filters and grew the colonies. We then lysed the filters [T. Maniatis et al., "Molecular Cloning—A Laboratory Manual", Cold Spring Harbor Laboratory (1982)] and screened them with our 16-mer oligonucleotide that we had labelled with $^{32}$P at the 5' end.

For this hybridization screening, we baked the filters, and then prehybridized and hybridized them in 6×SSC at 30° C. overnight. This hybridization resulted in a differential hybridization pattern: non-mutants have a two-base pair mismatch with the 16-mer probe and therefore hybridize poorly to it; mutants match the probe perfectly and thus hybridize strongly to it. Accordingly, we varied our washing temperatures (30°, 40°, 45° C.) to distinguish the two types of hybridization and to pick the colonies whose DNA strongly hybridized to the 16-mer probe.

We then analyzed the plasmid DNA from minipreps of these selected colonies by restriction with BanII and StuI and selected those that had lost a BanII site, but gained a StuI site. We used this restriction analysis to permit rapid screening of the clones. We also theorized that if the restriction site mutation was present in the prepared DNA, the DNA was more likely also to contain the Lys to Ile (A to T) mutation. However, we confirmed the presence of that latter mutation in our selected clones by Maxam-Gilbert DNA sequencing.

To prepare the modified t-PA DNA sequences of this invention, we substituted our modified 472 base pair EcoRI t-PA fragment for the unmodified fragment in a variety of expression vectors that had proven useful in producing unmodified t-PA in hosts transformed with those systems.

For example, in one such construction, we restricted pTPA55, an expression vector having the t-PA cDNA coding sequence under the control of a trp expression control sequence with EcoRI and inserted our EcoRI modified t-PA fragment. The resulting expression vector pTPA55 (Lys 277→Ile) in *E.coli* produced a low level of t-PA as detected by Western blots using anti t-PA antibodies (rabbit) and goat antirabbit antibodies conjugated with horseradish peroxidase and a colorimetric assay.

To improve the level of expression of our modified t-PAs, the modified DNA sequences of this invention may be transferred to other expression vectors and hosts. For example, we transferred our DNA sequence coding for t-PA (Lys 277→Ile) to expression system pTPA102 that produced unmodified t-PA under the control of a TRC expression system in *E.coli* SG 20251 at high levels (1%). For this construction, we restricted pTPA55 (Lys 277→Ile) and pTPA102 with NcoI and HindIII and ligated the appropriate fragments together.

The resulting plasmid pTPA102 (Lys 277→Ile), when transfected into *E.coli.* SG 20251 (a gift of Susan Gottesman), afforded the production of about 1% of our modified t-PA (Lys 277→Ile) on culturing of the transformed host in the presence of 50 μg/ul ampicillin. This level of t-PA was detectable by Western blots as before.

Protein sequencing of the amino terminal end of the modified t-PA produced in the above culture demonstrated that no detectable f-Met remained, the methonine apparently being clipped during synthesis in *E.coli.* In addition, about 20% of the molecules had lost their first three amino acids (Gly-Ala-Arg) because in those molecules the initial amino acid was serine.

We also assayed the comparative activity of the single and double chain forms of our modified t-PA produced in the above culture. In this assay, we observed an about 25X increase in activity in going from the single chain to the two chain form. In comparison only a 5-8X increase in activity is observed in the same assay between the single and two chain forms of unmodified recombinant t-PA. Accordingly, our modified t-PA is substantially inactive in the single chain form.

Although we have described the preparation and use of one modified DNA sequence of this invention, it should be understood that DNA sequences which because of the degeneracies of the genetic code on expression code for the same modified t-PAs as our DNA sequences are also included within the scope of this invention. For example, a DNA sequence having only the single A to T mutation (Lys 277→Ile), but not the second mutation (BanII→StuI), is part of this invention.

It should also be understood that other replacements and deletions to modify the positively charged 277 lysine in native or recombinant t-PAs are also part of this invention. These include, for example, other mutations where the 277 lysine is changed to another amino acid residue selected from the group of any amino acid, except His, Arg and Lys.

Microorganisms, recombinant DNA molecules and the modified t-PA DNA coding sequences of this invention and starting materials useful in preparing them are exemplified by cultures deposited in the culture collection of the American Type Culture Collection, Rockville, Md. on Aug. 21, 1984, and identified there as t-PA-A through D:

A: *E.coi* JA221 (pTPA25)
B: *E.coli* JA221 (pTPA55)
C: *E.coli* JA221 (pTPA102)
D: *E.coli* JA221 (pTPA102) (Lys 277→Ile)

Culture t-PA-E deposited on Aug. 27, 1984 is there identified as follows:

E: *E.coli* SG 20251 (pTPA102) (Lys 277→Ile) These cultures were assigned ATCC accession numbers ATCC 39808, 39809, 39810, 39811 and 39821, respectively.

While we have hereinbefore presented a number of embodiments of this invention, it is apparent that our basic construction can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

We claim:

1. An isolated DNA fragment containing a DNA sequence coding for human t-PA (Lys 277→X), wherein X is selected from the group consisting of one or more amino acid substitutions and deletions at the 277 Lys residue that prevents any substantial complexation between amino acid 277 and amino acid 194 in the single chain form of said t-PA.

2. The DNA fragment according to claim 1, wherein X is selected from the group consisting of at least one amino acid substitution, said amino acid being characterized by the absence of any substantial positive charge, and at least one amino acid deletion that removes any substantial positive charge from the 277 lysine in the single chain form of said t-PA.

3. The DNA fragment according to claim 2, wherein said amino acid substitution is selected from the group consisting of Phe, Leu, Ile, Met, Val, Ser, Pro, Thr, Ala, Tyr, Asn, Glu, Cys, Trp and Gly.

4. The DNA fragment according to claim 3, wherein said amino acid substitution is Ile.

5. A recombinant DNA molecule comprising a DNA fragment selected from the group consisting of the DNA fragment of any one of claims 1 to 4, said DNA fragment being operatively linked to an expression control sequence in said recombinant DNA molecule.

6. The recombinant DNA molecule according to claim 5, selected from the group consisting of pTPA55-(Lys 277→Ile) and pTPA 102(Lys 277→Ile).

7. A unicellular host transformed with a recombinant DNA molecule according to claim 5.

8. The unicellular host according to claim 7, selected from the group consisting of bacteria, yeasts and other fungi, and animal and plant cells in tissue culture.

9. The unicellular host ccording to claim 7, said host being designated *E. coli* SG 20251 pTPA102) (Lys 277→Ile).

10. Human tissue plasminogen activator having the formula t-P A (Lys 277→X), wherein X is selected from the group consisting of one or more amino acid substitutions and deletions at the 277 Lys residue that prevents any substantial complexation between amino acid 277 and amino acid 194 in the single chain form of said t-PA.

11. The plasminogen activator according to claim 10, wherein X is selected from the group consisting of at least one amino acid substitution, said amino acid being characterized by the absence of any substantial positive charge, and at least one amino acid deletion that removes any substantial positive charge from the 277 lysine in the single chain form of said t-PA.

12. The plasminogen activator according to claim 11, wherein said amino acid is selected from the group consisting of Phe, Leu, Ile, Met, Val, Ser, Pro, Thr, Ala, Tyr, Asn, Glu, Cys, Trp and Gly.

13. Human t-PA (Lys 277→Ile).

14. The t-PA according to any one of claims 10 to 13 unaccompanied by native glycosylation.

15. A method for producing human t-PA (Lys 277→X), wherein X is selected from the group consisting of one or more amino acid substitutions, and deletions at the 277 Lys residue that prevents any substantial complexation between amino acid 277 and amino acid 194 in the single chain form of said t-pA, said method comprising the step of culturing a unicellular host transformed with at least one recombinant DNA molecule, said molecule comprising a DNA sequence coding for t-PA (Lys 277→X), said DNA sequence being operatively linked to an expression control sequence in said molecule.

16. The method according to claim 15, wherein X is selected from the group consisting of at least one amino acid substitution, said amino acid being characterized by the absence of any substantial positive charge, and at least one amino acid deletion that removes any substantial positive charge from the 277 lysine in the single chain form of said t-PA.

17. The method according to claim 16, wherein said amino acid substitution is selected from the group consisting of Phe, Leu, Ile, Met, Val, Ser, Pro, Thr, Ala, Tyr, Asn, Glu, Cys, Trp and Gly.

18. The method according to claim 17, wherein said amino acid substitution is Ile.

19. The method according to any one of claims 15 to 18, wherein said host is selected from the group consisting of strains of bacteria, yeasts and other fungi, and animal and plant cells in tissue culture.

20. The method according to claim 19, wherein said transformed host is E.coli SG 20251 (pTPA 102) (Lys 277→Ile).

21. The method according to any one of claims 15–18, wherein said expression control sequence is selected from the group consisting of the lac system, and trp system, the operator and promoter systems of phage λ, the TAC system, the TRC system, the β-lac system, the SV40 system, the promoters of yeast glycolytic enzymes, the promoters of yeast α-mating factors, the promoters of yeast acid phosphatases, and other sequences that control the expression of genes of prokaryotic or eukaryotic cells or their viruses.

* * * * *